United States Patent
Takaki et al.

(10) Patent No.: US 6,211,225 B1
(45) Date of Patent: Apr. 3, 2001

(54) HETEROCYCLIC AMINOPYRROLIDINE DERIVATIVES AS MELATONERGIC AGENTS

(75) Inventors: Katherine S. Takaki, Middletown; Guanglin Luo, Madison; Stephen R. Bertenshaw, Cheshire, all of CT (US)

(73) Assignee: Bristol-Meyers Squibb, Princeton, NJ (US)

( * ) Notice: Subject to any disclaimer, the term of this patent is extended or adjusted under 35 U.S.C. 154(b) by 0 days.

(21) Appl. No.: 09/587,928

(22) Filed: Jun. 6, 2000

Related U.S. Application Data

(60) Provisional application No. 60/141,894, filed on Jun. 30, 1999.

(51) Int. Cl.[7] ................ A61K 31/4025; A61P 25/20; C07D 405/02
(52) U.S. Cl. .............. 514/422; 548/525; 548/526
(58) Field of Search ................... 548/525, 526; 514/422

(56) References Cited

U.S. PATENT DOCUMENTS

| | | |
|---|---|---|
| 5,753,709 | 5/1998 | Keavy et al. |
| 5,856,529 | 1/1999 | Catt et al. |

FOREIGN PATENT DOCUMENTS

| | | |
|---|---|---|
| 420 064 | 4/1991 | (EP) |
| 506 539 | 9/1992 | (EP) |
| 527 687 | 2/1993 | (EP) |
| 562 956 | 9/1993 | (EP) |
| 708 099 | 4/1996 | (EP) |
| WO 94/07487 | 4/1994 | (WO) |
| WO 95/17405 | 6/1995 | (WO) |
| WO 95/29173 | 11/1995 | (WO) |
| WO 97/43272 | 11/1997 | (WO) |

OTHER PUBLICATIONS

Arendt, J., et al., "Alleviation of Jet Lag by Melatonin: Preliminary Results of Controlled Double Blind Trial", *Br. Med. J.*, 292, pp. 1170–1172 (May 1986).

Cassone, V. M., et al., "Dose–Dependent Entrainment of Rat Circadian Rhythms by Daily Injection of Melatonin", *J. Biol. Rhythms*, 1, (3), pp. 219–229 (1986).

Reppert, S. M., et al., "Cloning and Characterization of a Mammalian Melatonin Receptor That Mediates Reproductive and Circadian Responses", *Neuron*, 13, pp. 1177–1185 (Nov., 1994).

Reppert, S. M., et al., "Molecular Characterization of a Second Melatonin Receptor Expressed in Human Retina and Brain: The $Mel_{1b}$ Melatonin Receptor", *Proc. Natl. Acad. Sci. USA*, 92, pp. 8734–8738 (Sep. 1995).

*Primary Examiner*—Joseph K. McKane
*Assistant Examiner*—Andrea M D'Souza
(74) *Attorney, Agent, or Firm*—Aldo A. Algieri

(57) ABSTRACT

There is provided a novel series of heterocyclic aminopyrrolidine compounds of Formula I

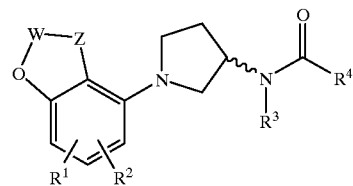

wherein $R^1$, $R^2$, $R^3$, $R^4$, W, Z and the wavy bond ~~ are as defined herein which bind to the human melatonin receptor and therefore are useful as melatonergic agents.

12 Claims, No Drawings

HETEROCYCLIC AMINOPYRROLIDINE DERIVATIVES AS MELATONERGIC AGENTS

CROSS-REFERENCE TO RELATED APPLICATIONS

This is a nonprovisional application which claims benefit of provisional application U.S. Ser. No. 60/141,894 filed Jun. 30, 1999.

BACKGROUND OF THE INVENTION

The invention pertains to novel substituted heterocyclic aminopyrrolidine derivatives having drug and bio-affecting properties and to their preparation, pharmaceutical formulations and use. In particular, the invention concerns benzodioxoles, benzofurans, dihydrobenzofurans, dihydrobenzodioxanes and related derivatives bearing substituted aminopyrrolidine groups. These compounds possess melatonergic properties that should make them useful in treating certain medical disorders.

Melatonin (N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

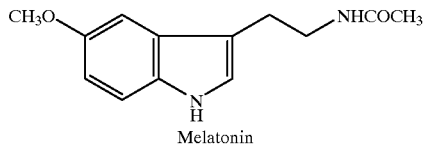
Melatonin

Recent evidence demonstrates that melatonin exerts its biological effects through specific receptors. Use of the biologically active, radiolabelled agonist [$^{125}$I]-2-iodomelatonin has led to the identification of high affinity melatonin receptors in the CNS of a variety of species. The sequences of two cloned human melatonin receptors have been reported [Reppert, et al., *Proc. Natl. Acad. Sci.* 92, p. 8734–8738, (1995) and Reppert, et al., *Neuron* 13, p. 1177–1185, (1994)]. In mammalian brain, autoradiographic studies have localized the distribution of melatonin receptors to a few specific structures. Although there are significant differences in melatonin receptor distribution even between closely related species, in general the highest binding site density occurs in discreet nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms,* 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487, published on Apr. 14, 1994.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, premenstrual syndrome, immune disorders, inflammatory articular diseases and neuroendocrine disorders.

Aside from simple indole derivatives of melatonin itself, various bicyclic structures have been prepared and their use as melatonin ligands disclosed. In general these bicyclic amide structures can be represented as:

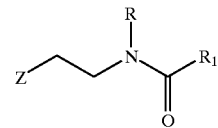

wherein Z is an aryl or heteroaryl system attached by a two carbon bridge to the amide group. Some specific examples follow.

Yous, et al. in European Patent Application EP-527,687A, published on February 17, 1993, disclose as melatonin ligands arylethylamines i,

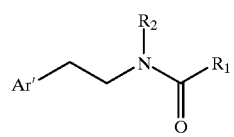

wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Yous, et al. in European Patent Application EP-506,539A, published on Sep. 30, 1992, claim ligands ii,

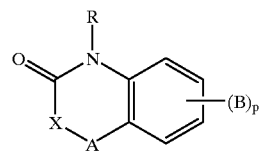

wherein A is oxygen or sulfur; X is a methylene group or a bond; and R is H or lower alkyl when p is 1 and B is defined by the radical iii,

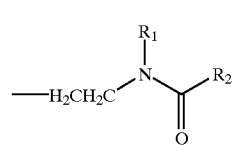

wherein $R_1$ is hydrogen or lower alkyl and $R_2$ is, inter alia, hydrogen, lower alkyl or cycloalkyl. Alternatively, R is defined by the radical iii when p is 0 or 1 and B is lower alkoxy.

Several naphthalene derivatives have also been disclosed as melatonin ligands.

Yous, et al. in European Patent Application EP-562,956A, published on Sep. 29, 1993, disclose amide and urea naphthalene derivatives iv,

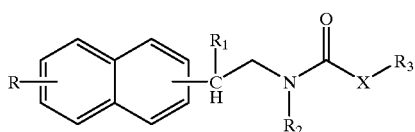

iv in which R is hydrogen or $OR_4$ wherein $R_4$ is, inter alia, hydrogen, alkyl, cycloalkyl, or cycloalkylalkyl; $R_1$ is hydrogen or $COOR_5$ wherein $R_5$ is hydrogen or alkyl; $R_2$ is hydrogen or alkyl; X is NH or a bond; and $R_3$ is, inter alia, alkyl, alkenyl, or cycloalkyl.

Horn and Dubocovich in European Patent Application EP-420,064A, published on Apr. 3, 1991, disclose 2-amidotetralins v as melatonin ligands,

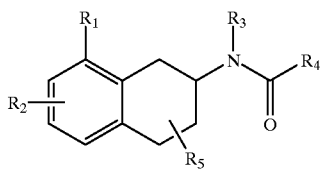

v wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Lesieur et al, in EP-708,099A, published Apr. 24, 1996, disclose compounds of structure vi, which are useful for the treatment of diseases caused by a melatonin imbalance.

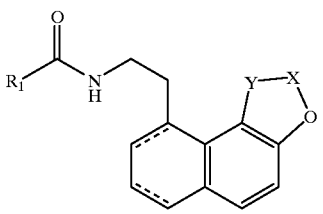

vi wherein === is a single or double bond; $R_1$=Me or MeNH; and X—Y=—CH(Me)—$CH_2$—, $CH_2CH(OH)$— or $(CH_2)_3$—.

North et al., in International Application WO 95/29173, published Nov. 2, 1995, disclose naphthalene derivatives of structure vii:

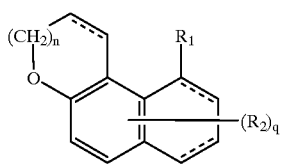

vii wherein $R_1$ is a group of the formula $CR_3R_4$ $(CH_2)$ $pNR_5COR_6$; $R_2$ is hydrogen, halogen, $C_{1-6}$ alkyl, $OR_7$ or $CO_2R_7$; and may be the same or different substituent when q is 2; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; $R_7$ is hydrogen or $C_{1-6}$ alkyl; n is zero, 1 or 2; p is an integer of 1, 2, 3 or 4; q is 1 or 2; and the dotted lines indicate the absence or presence of an additional bond. The North et al. compounds are taught to treat chronobiological disorders.

In International Application WO 95/17405, published on Jun. 29, 1995, North et al., disclose compounds of structure viii and teach their use in the treatment of conditions related to the melatonin system.

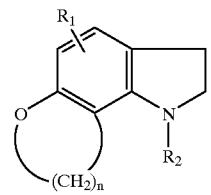

viii wherein $R_1$ is hydrogen, halogen or $C_{1-6}$ alkyl; $R_2$ is a group of formula —$CR_3R_4(CH_2)_pNR_5COR_6$; $R_3$, $R_4$ and $R_5$, which may be the same or different, are hydrogen or $C_{1-6}$ alkyl; $R_6$ is $C_{1-6}$ alkyl or $C_{3-7}$ cycloalkyl; n is an integer of 2, 3 or 4; and p is an integer of 1, 2, 3 or 4.

Keavy, et al., in U.S. Pat. No. 5,753,709, issued on May 19, 1998, disclose compounds of formula ix which are useful as melatonergic agents,

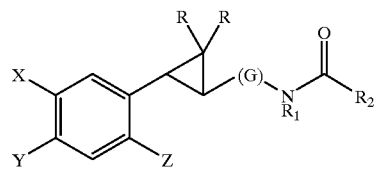

ix wherein X represents halogen, hydrogen, $C_{1-4}$alkyl or $OR_5$ wherein, inter alia, $R_5$ is hydrogen, $C_{1-20}$alkyl or $C_{4-20}$alkylcycloalkyl; Y represents hydrogen or halogen; X represents inter alia, hydrogen, halogen, cyano or aryl; R represents hydrogen, halogen or $C_{1-4}$alkyl or; $R_1$ represents hydrogen, $C_{1-4}$alkyl or benzyl and $R_2$ represents $C_{1-6}$alkyl, $C_{2-6}$alkenyl, $C_{3-6}$cycloalkyl, $C_{2-4}$alkoxyalkyl, $C_{1-4}$trifluoromethylalkyl or $C_{2-8}$alkylthioalkyl.

In International Application WO 97/43272, published on Nov. 20, 1997, Ellis, et al., disclose compounds of structure x as melatonin ligands.

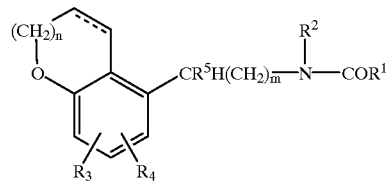

x wherein $R^1$ and $R^2$ represent hydrogen, $C_{1-6}$alkyl, $C_{3-7}$cycloalkyl or aryl, $R^3$ and $R^4$ represent hydrogen, halogen or $C_{1-6}$alkyl or substituted aryl, $R^5$ represents hydrogen or $C_{1-6}$alkyl, n is 0–2, m is 1–4 and the dotted line represents an additional bond.

Catt, et al., in U.S. Pat. No. 5,856,529, issued on Jan. 5, 1999, disclose compounds of formula xi which are useful as melatonergic agents,

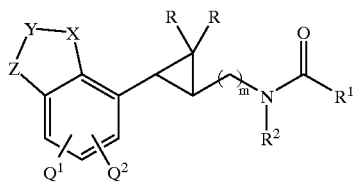

xi wherein $Q^1$ and $Q^2$ represent hydrogen or halogen; X represents $CH_2$, CH or oxygen; Y represents $CR^3$, $CR^3R^4$ or $(CH_2)_n$ with n=1–4; Z represents $CH_2$, CH or oxygen; R represents hydrogen, halogen or $C_{1-4}$ alkyl; m is 1 or 2; $R^2$ represents hydrogen or C: $_4$ alkyl and $R^1$ represents $C_{1-6}$ alkyl, $C_{3-6}$ cycloalkyl, $C_{1-3}$ haloalkyl, $C_{1-6}$ alkylamino, $C_{2-6}$ alkenyl, $C_{1-4}$ alkoxy($C_{1-4}$)alkyl, $C_{1-4}$ alkylthio($C_{1-4}$)alkyl or $C_{1-4}$ trifluoromethylalkyl.

The foregoing disclosures do not teach or suggest the novel melatonergic heterocyclic aminopyrrolidine derivatives of the present invention. The novel compounds of the present invention display melatonergic agonist activity.

SUMMARY OF THE INVENTION

The invention provides a novel series of aminopyrrolidine compounds of Formula I

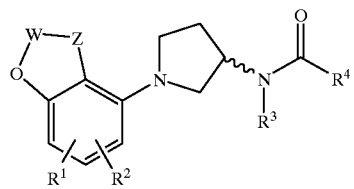

I wherein $R^1$, $R^2$, $R^3$, $R^4$, W, Z and the wavy bond ∿∿ are as defined below, including nontoxic pharmaceutically acceptable salts, hydrates and solvates thereof which bind to the human melatonergic receptor and therefore are useful as melatonergic agents in the treatment of sleep disorders, seasonal depression, shifts in circadian cycles, melancholia, stress, appetite regulation, benign prostatic hyperplasia and related conditions.

DETAILED DESCRIPTION OF THE INVENTION

The invention provides a novel series of heterocyclic aminopyrrolidine compounds having the formula:

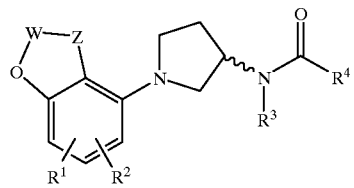

I wherein
the wavy bond ∿∿ represents the racemate, the (R)-enantiomer or the (S)-enantiomer;

$R^1$ and $R^2$ each are independently hydrogen or halogen;
W is $CR^5$, $CR^5R^6$ or $(CH_2)n$, with n=1–2;
Z is $CH_2$, CH or oxygen;
$R^3$ is hydrogen or $C_{1-4}$ alkyl;
$R^4$ is $C_{1-6}$ alkyl, $C_{3-6}$ cycloalkyl, $C_{1-3}$ haloalkyl, $C_{2-6}$ alkenyl, $C_{1-6}$ alkyamino, $C_{3-6}$ cycloalkylamino, di($C_{1-4}$)alkylamino, $C_{1-4}$ alkoxy ($C_{1-4}$)alkyl, $C_{1-4}$ alkylthio($C_{1-4}$)alkyl or $C_{1-4}$ trifluoromethyl($C_{1-2}$)alkyl; and
$R^5$ and $R^6$ each are independently hydrogen or $C_{1-4}$ alkyl; or a nontoxic pharmaceutically acceptable salt, hydrate or solvate thereof.

The present invention also provides a method for the treatment of sleep disorders and related conditions, which comprises administering a therapeutically effective amount of a compound of Formula I or a nontoxic pharmaceutically acceptable salt, solvate or hydrate thereof.

$R^1$ and $R^2$ are selected from H and halogen (i.e., bromine, chlorine, iodine or fluorine). It is most preferred that $R^1$ and $R^2$ be H or chlorine.

W is $CR^5$ (when a double bond is present), $CR^5R^6$ or —$(CH_2)_n$— and n is preferably 1 or 2.

Z may be $CH_2$, CH (when a double bond is present) or oxygen.

When W and Z are $CH_2$, the compound is a dihydrobenzofuran. When W and Z are CH, the compound is a benzofuran. When Z is oxygen and W is $CH_2$, the compound is a benzodioxole. When Z is oxygen and W is $(CH_2)_2$, the compound is a benzodioxane. Compounds in which W and Z are $CH_2$ are preferred.

$R^4$ is one of several types of groups. $R^4$ is selected from $C_{1-6}$ alkyl, $C_{3-6}$ cycloalkyl, $C_{1-3}$ haloalkyl, $C_{2-6}$ alkenyl, $C_{1-6}$ alkylamino, $C_{3-6}$ cycloalkylamino, di($C_{1-4}$)alkylamino, $C_{1-4}$ alkoxy($C_{1-4}$)alkyl, $C_{1-4}$ trifluoromethyl($C_{1-2}$)alkyl and $C_{1-4}$ alkylthio($C_{1-4}$)alkyl groups. $R^4$ is preferably $C_{1-6}$ alkyl, $C_{1-6}$ alkylamino, $C_{3-6}$ cycloalkyl, or $C_{3-6}$ cycloalkylamino.

$R^3$ is hydrogen or $C_{1-4}$ alkyl. $R^3$ is preferably hydrogen.

$R^5$ and $R^6$ are hydrogen or $C_{1-4}$ alkyl. It is preferred that $R^5$ and $R^6$ both be hydrogen. It is also preferred that $R^5$ is hydrogen and $R^6$ is methyl. When $R^5$ is hydrogen and $R^6$ is methyl, both enantiomers and racemate are preferred.

The terms "$C_{1-4}$ alkyl", "$C_{1-6}$ alkyl", and "$C_{1-4}$ alkoxy" as used herein and in the claims mean a straight or branched chain alkyl or alkoxy group such as methyl, ethyl, propyl, isopropyl, butyl, isobutyl, t-butyl, amyl, hexyl and the like.

The term "$C_{2-6}$ alkenyl" means a straight or branched alkylene group such as ethylene, propylene, methylethylene, butylene, pentylene and the like.

"W—Z" refers to a single bond or double bond attachment when defined by the substituents W and Z.

The term "$C_{3-6}$ cycloalkyl" groups are monovalent cyclic moieties containing at least 3 carbon atoms and conforming to the formula $C_xH_{(2x-1)}$, with x being the number of carbon atoms present. The cyclopropyl group is a preferred cycloalkyl moiety.

The term "haloalkyl" includes straight and branched chain hydrocarbon radicals bearing from 1 to 3 halogen moieties. "Halogen" means F, Cl, Br or I. Preferred halogens in $R^1$, $R^2$ and haloalkyl moieties of $R^4$ include F and Cl.

The term "wavy bond ∿∿" which is attached to the pyrrolidine group as used herein in the chemical structures and in the claims is intended to include the racemic mixture as well as the two individual stereoisomers designated herein as (R)-enantiomer and (S)-enantiomer.

The term "nontoxic pharmaceutically acceptable salt" as used herein and in the claims is intended to include nontoxic inorganic acids such as hydrochloric, hydrobromic, hydroiodic, sulfuric, nitric, phosphoric and the like, and nontoxic organic acids such as acetic, benzoic, fumaric, cinnamic, mandelic, succinic, citric, maleic, lactic and the like.

The term "hydrate or solvate thereof" as used herein and in the claims is intended to include hydrated forms such as monohydrate, dihydrate, hemihydrate, sesquihydrate, trihydrate, tetrahydrate and the like as well as solvated forms. The products may be true hydrates, while in other cases, the products may merely retain adventitious water or be a mixture of water plus some adventitious solvent. It should be appreciated by those skilled in the art that hydrated and/or solvated forms are equivalent to unsolvated forms and are intended to be encompassed within the scope of the present invention.

Additionally, compounds of Formula I encompass all pharmaceutically acceptable solvates, particularly hydrates, thereof. The present invention also encompasses diastereomers as well as optical isomers, e.g. mixtures of enantiomers including racemic mixtures, as well as individual enantiomers and diastereomers, which arise as a consequence of structural asymmetry in certain compounds of Formula I. Separation of the individual isomers or selective synthesis of the individual isomers is accomplished by application of various methods which are well known to practitioners in the art.

As the compounds of the present invention possess an asymmetric carbon atom at the 3-position of the pyrrolidine ring, the present invention includes the racemate as well as the individual enantiometric forms of the compounds of Formula I as described herein and in the claims. The use of a single designation such as (R) or (S) is intended to include mostly one stereoisomer. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. Although the enantiomeric forms may be separated by fractionation through chiral high pressure liquid chromatography columns, the optically active enantiomers of the compounds of Formula I are preferably prepared by stereoselective synthetic procedures described herein.

The present invention also provides a method for treating a mammal, including man, afflicted with disorders associated with melatonergic receptors, especially circadian rhythm-related disorders which comprises administering a therapeutically effective amount of a compound of Formula I or a nontoxic pharmaceutically acceptable salt, hydrate or solvate thereof.

In the method of the present invention, the term "therapeutically effective amount" means the total amount of each active component of the method that is sufficient to show a meaningful patient benefit, i.e., alleviating or or ameliorating disorders associated with melatonergic receptors. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims meaning alleviating or ameliorating stress, sleep disorders, seasonal depression, appetite regulation, shifts in circadian cycles, melancholia, benign prostate hyperplasia, inflammatory articular diseases, headaches and related conditions associated with melatonergic action.

One group of preferred compounds include the benzofurans, dihydrobenzofurans and benzopyrans of Formula I wherein the group, W—Z consists of —CH$_2$—CH$_2$—, —CH=CH—, —C(CH$_3$)$_2$—CH$_2$—, —CH(CH$_3$)—CH$_2$—, —C(CH$_3$)=CH— and —(CH$_2$)$_2$—CH$_2$—.

Some preferred compounds of this group include:
(S)-N-[N-(2,3-dihydrobenzofuran-4-yl)-pyrrolidin-3-yl] acetamide;
(R)-N-[N-(2,3-dihydrobenzofuran-4-yl)-pyrrolidin-3-yl] acetamide;
(S)-N-[N-(2,3-dihydrobenzofuran-4-yl)-pyrrolidin-3-yl] propanamide;
(R)-N-[N-(2,3-dihydrobenzofuran-4-yl)-pyrrolidin-3-yl] propanamide;
(S)-N-[N-(2,3-dihydrobenzofuran-4-yl)-pyrrolidin-3-yl] butyramide;
(R)-N-[N-(2,3-dihydrobenzofuran-4-yl)-pyrrolidin-3-yl] butyramide;
(S)-N-[N-(2,3-dihydrobenzofuran-4-yl)-pyrrolidin-3-yl] isobutyramide;
(R)-N-[N-(2,3-dihydrobenzofuran-4-yl)-pyrrolidin-3-yl] isobutyramide;
(S)-N-[N-(2,3-dihydrobenzofuran-4-yl)-pyrrolidin-3-yl] cyclopropane carboxamide;
(R)-N-[N-(2,3-dihydrobenzofuran-4-yl)-pyrrolidin-3-yl] cyclopropane carboxamide;
(S)-N-[N-(2,3-dihydrobenzofuran-4-yl)-pyrrolidin-3-yl] methoxyacetamide;
(S)-N-[N-(2H-2,3-dihydrobenzopyran-5-yl)-pyrrolidin-3-yl]propanamide;
(R)-N-[N-(2,3-dihydrobenzofuran-4-yl)-pyrrolidin-3-yl]-N'-methyl urea;
(S)-N-[N-(2,3-dihydrobenzofuran-4-yl)-pyrrolidin-3-yl]-N'-methyl urea;
(S)-N-[N-(2,3-dihydrobenzofuran-4-yl)-pyrrolidin-3-yl]-N'-ethyl urea;
(R)-N-[N-(2,3-dihydrobenzofuran-4-yl)-pyrrolidin-3-yl]-N'-ethyl urea;
(S)-N-[N-(2,3-dihydrobenzofuran-4-yl)-pyrrolidin-3-yl]-N'-n-propyl urea;
(R)-N-[N-(2,3-dihydrobenzofuran-4-yl)-pyrrolidin-3-yl]-N'-n-propyl urea;
(S)-N-[N-(2H-2,3-dihydrobenzopyran-5-yl)-pyrrolidin-3-yl]-N'-ethyl urea;
(R)-N-[N-(2,3-dihydrobenzofuran-4-yl)-pyrrolidin-3-yl]-N'-cylopropyl urea;
(S)-N-[N-(2,3-dihydrobenzofuran-4-yl)-pyrrolidin-3-yl]-N'-cylopropyl urea;
(S)-N-[N-(2,3-dihydrobenzofuran-4-yl)-pyrrolidin-3-yl]-N',N'-dimethyl urea;
(R)-N-[N-(2,3-dihydrobenzofuran-4-yl)-pyrrolidin-3-yl]-N',N'-dimethyl urea;
(S)-N-[N-(5-chloro-2,3-dihydrobenzofuran-4-yl)-pyrrolidin-3-yl]acetamide;
(S)-N-[N-(5,7-dichloro-2,3-dihydrobenzofuran-4-yl)-pyrrolidin-3-yl]-acetamide;
(S)-N-[N-(5-chloro-2,3-dihydrobenzofuran-4-yl)-pyrrolidin-3-yl]butyramide;
(S)-N-[N-(5,7-dichloro-2,3-dihydrobenzofuran-4-yl)-pyrrolidin-3-yl]-butyramide;
(S)-N-[N-(5-chloro-2,3-dihydrobenzofuran-4-yl)-pyrrolidin-3-yl]-cyclopropane carboxamide;
(S)-N-[N-(5,7-dichloro-2,3-dihydrobenzofuran-4-yl)-pyrrolidin-3-yl]-cyclopropane carboxamide;
(S)-N-[N-(5-chloro-2,3-dihydrobenzofuran-4-yl)-pyrrolidin-3-yl]-N'-ethyl urea;

(R)-N-[N-(5-chloro-2,3-dihydrobenzofuran-4-yl)-pyrrolidin-3-yl]-N'-ethyl urea;
(S)-N-[N-(5,7-dichloro-2,3-dihydrobenzofuran-4-yl)-pyrrolidin-3-yl]-N'-ethyl urea; and
(R)-N-[N-(5,7-dichloro-2,3-dihydrobenzofuran-4-yl)-pyrrolidin-3-yl]-N'-ethyl urea.

Another group of preferred compounds include the benzodioxoles and benzodioxanes of Formula I wherein the group W—Z consists of —CH$_2$—O— and —(CH$_2$)$_2$—O—, respectively.

R)-N-[N-(2,3-methylenedioxyphen-1-yl)-pyrrolidin-3-yl] propanamide;
(S)-N-[N-(2,3-dihydro-1,4-benzodioxin-5-yl)-pyrrolidin-3-yl]acetamide;
(S)-N-[N-(2,3-dihydro-1,4-benzodioxin-5-yl)-pyrrolidin-3-yl]propanamide;
(S)-N-[N-(2,3-dihydro-1,4-benzodioxin-5-yl)-pyrrolidin-3-yl]butyramide;
(S)-N-[N-(2,3-dihydro-1,4-benzodioxin-5-yl)-pyrrolidin-3-yl]cyclopropane carboxamide;
(R)-N-[N-(2,3-methylenedioxyphen-1-yl)-pyrrolidin-3-yl]-N'-methyl urea;
(R)-N-[N-(2,3-methylenedioxyphen-1-yl)-pyrrolidin-3-yl]-N'-ethyl urea;
(S)-N-[N-(2,3-dihydro-1,4-benzodioxin-5-yl)-pyrrolidin-3-yl]-N'-methyl urea;
(S)-N-[N-(2,3-dihydro-1,4-benzodioxin-5-yl)-pyrrolidin-3-yl]-N'-ethyl urea; and
(S)-N-[N-(2,3-dihydro-1,4-benzodioxin-5-yl)-pyrrolidin-3-yl]-N'-n-propyl urea.

The compounds of Formula I may be prepared by various procedures such as those illustrated herein in the examples, in the reaction schemes and variations thereof which would be evident to those skilled in the art. The various aminopyrrolidine derivatives of Formula I may advantageously be prepared as illustrated in Reaction Schemes.

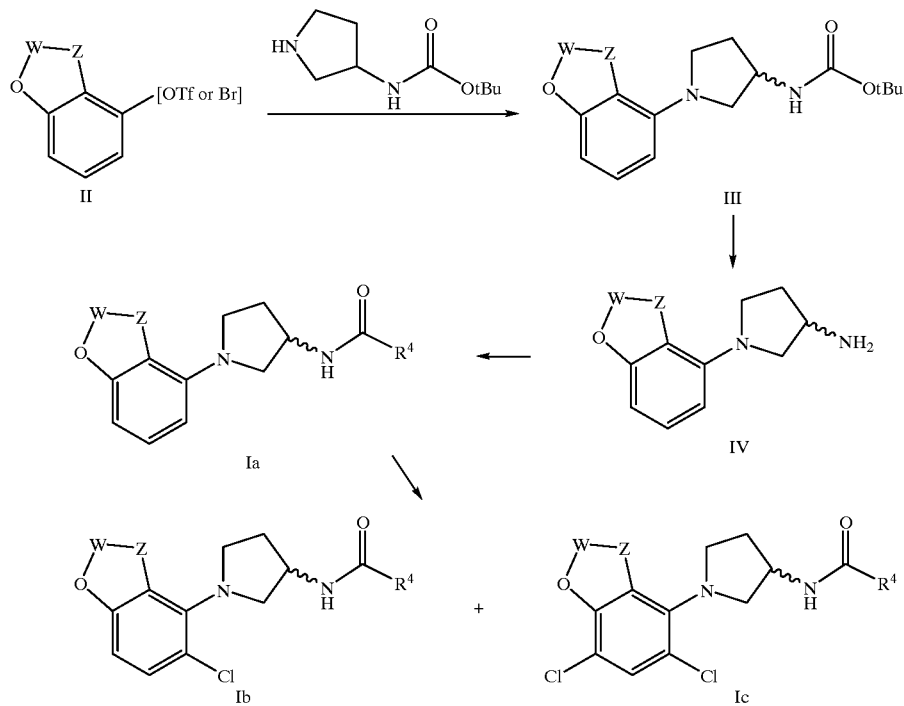

Reaction Scheme 1

The starting triflates of Formula II can be prepared by methods well known to those skilled in the art from the corresponding phenols. Conversion to the pyrrolidines of Formula III can be accomplished by palladium-mediated coupling to (R or S)-3-(tert-butoxycarbonylamino) pyrrolidine using a Pd catalyst like tetrakis (triphenylphosphine)palladium (0), palladium(II) acetate, dichlorobis(triphenylphosphine)palladium (II), and the like in the presence of a co-catalyst like 2,2'-bis (diphenylphosphino)-1,1'-binaphthyl (BINAP) or tri-o-tolylphosphine and a base like cesium carbonate, potassium carbonate, sodium methoxide, potassium t-butoxide and the like in an inert solvent such as toluene, benzene, dioxane, tetrahydrofuran or dimethylformamide. Hydrolysis of the protecting group using standard methods well known to those skilled in the art provides the penultimate amines of Formula IV. Further reaction of amines of Formula IV with acylating reagents provides compounds of Formula Ia. Suitable acylating agents include carboxylic acid halides, anhydrides, acyl imidazoles, alkyl isocyanates, alkyl isothiocyanates and carboxylic acids in the presence of condensing agents such as carbonyl imidazole, carbodiimides, and the like. Treatment of compounds of Formula Ia with chlorinating agents like N-chlorosuccinimide provides compounds of Formula Ib and Ic.

Biological Activity of the Compounds

The compounds of the invention are melatonergic agents. They have been found to bind human melatonergic receptors expressed in a stable cell line with good affinity. Further, the compounds are agonists as determined by their ability, like melatonin, to block the forskolin-stimulated accumulation of cAMP in certain cells. Due to these properties, the compounds and compositions of the invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia, benign prostatic hyperplasia, inflammatory articular diseases, headaches, and related conditions.

Melatonergic Receptor Binding Activity

1. Reagents:
    (a) TME=50 mM Tris buffer containing 12.5 mM $MgCl_2$, and 2 mM EDTA, pH 7.4 at 37° C. with concentrated HCl.
    (b) Wash buffer: 20 mM Tris base containing 2 mM $MgCl_2$, pH 7.4 at room temperature.
    (c) $10^{-4}$ M melatonin ($10^{-5}$ M final concentration).
    (d) 2-$[^{125}I]$-iodomelatonin, 0.1 M final concentration 2. Membrane Homogenates:

The melatonin $ML_{1a}$ receptor cDNA was subcloned into pcDNA3 and introduced into NIH-3T3 cells using Lipofectamine. Transformed NIH-3T3 cells resistant to geneticin (G-418) were isolated, and single colonies expressing high levels of 2$[^{125}I]$-iodomelatonin binding were isolated. Cells are maintained in DMEM supplemented with 10% calf serum and G-418 (0.5 g/liter). Cells are grown to confluency in T-175 flasks, scraped using Hank's balanced salt solution, and frozen at -80° C. For preparing membrane homogenates, pellets are thawed on ice, and resuspended in TME buffer in the presence of 10 $\mu$g/ml aprotinin and leupeptin, and 100 $\mu$M phenylmethylsulfonylfluoride. The cells were then homogenized using a dounce homogenizer, and centrifuged. The resulting pellet was resuspended with dounce homogenizer in TME (supplemented with the above protease inhibitors) and frozen. On the day of assay, the small aliquot was thawed on ice and resuspended in ice cold TME (1:50–1:100 v/v) and held on ice until assayed.

3. Incubation:

37° C. for 1 hour. Reaction is terminated by filtration. Filters are washed 3 times.

4. References:

Reppert, et al., *Neuron*, 13, p. 1177–1185 (1994).

TABLE 1

| Example No. | Melatonin Binding Affinity $(IC_{50})^a$ |
|---|---|
| 4 | + |
| 10 | ++ |
| 11 | ++ |
| 13 | ++ |
| 14 | + |
| 20 | ++ |
| 21 | ++ |
| 28 | + |
| 30 | + |
| 32 | + |
| 35 | ++ |
| 36 | ++ |

$^a$= $IC_{50}$ values for $ML_{1a}$ human melatonin receptor binding
++ = <10 nM
+ = 10–200 nM The compounds of the present invention have affinity for receptors of the endogenous pineal hormone, melatonin, as determined in a receptor binding assays described above in Table 1 for the $ML_{1a}$ (human) receptors. Melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer, benign prostatic hyperplasia, immune disorders and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

In making pharmaceutical compositions containing compounds of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The dosage of the compounds of Formula I to achieve a therapeutic effect will depend not only on such factors as the age, weight and sex of the patient and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

The compositions are preferably formulated in a unit dosage form, each dosage containing from about 0.1 to 100 mg, more usually 1 to 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 10 mg/day, in single or divided doses, is preferred. Generally, the compounds of the invention may be used in treating sleep and related disorders in a manner similar to that used for melatonin.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

In the following examples, used to illustrate the foregoing synthetic processes, all temperatures are expressed in degrees Celsius and melting points are uncorrected. Proton magnetic resonance ($^{1}$H NMR) and carbon magnetic resonance ($^{13}$C NMR) spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. The infrared (IR) spectral descriptions include only absorption wave numbers ($cm^{-1}$) having functional group identification value. The IR determinations were employed using the compound neat as a film or by employing potassium bromide (KBr) as diluent. Optical rotations $[\alpha]_D^{25}$ were determined in the solvents and concentration indicated. Low resolution mass spectra (MS) are reported as the apparent molecular weight $(M+H)^+$. The elemental analyses are reported as percent by weight.

Preparation of Intermediates of Formula II
(2,3-Dihydrobenzofuran-4-yl)Trifluoromethane Sulfonate
Step 1: 2-Bromoresorcinol

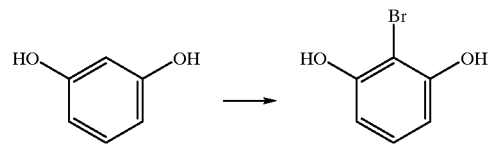

Bromine (0.363 L) was added dropwise over 2 hours to a solution of resorcinol (250 g) in dichloromethane (3.5 L). The solution was stirred at room temperature for 18 hours at which time approximately 1 L of the dichloromethane was removed by distillation. MeOH was added and the distillation continued in this manner until all of the dichloromethane was removed and the solution contained approximately 1.5 L of MeOH. To this was added a solution of NaOH (181.5 g) and $Na_2SO_3$ (573 g) in $H_2O$ (7.5 L). The resulting mixture was stirred at ambient temperature for 1 hour. The solution was then acidified to pH=2 with concentrated HCl (75 mL) and extracted with tert-butyl methyl ether (TBME) (2×1 L). The combined organic layers were treated with activated charcoal (20 g) and filtered through Celite; the Celite was washed with an additional 500 mL of TBME. The solvent was then removed in vacuo. The resulting crude 2-bromoresorcinol was dissolved in a minimum amount of ethyl acetate and filtered through silica gel eluting with a gradient from 20% to 40% ethyl acetate in hexanes yielding 2-bromoresorcinol (122 g). m.p. 86–88°.

Step 2: 2,6-Di(2-Chloroethoxy)Bromobenzene

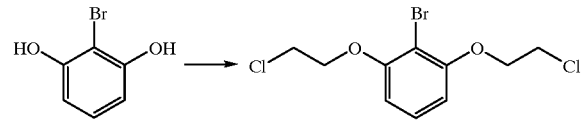

Potassium carbonate (536 g), sodium iodide (9.76 g), and sodium metabisulfate (12.2 g) were suspended in dichloromethane (1.53 L) and DMF (0.4 L) and heated to 80° C. A solution of 2-bromoresorcinol (122.3 g) in DMF (0.4 L) was then added dropwise over 2 hours. The reaction was stirred at 80° C. for 20 hours, cooled to ambient temperature and filtered through a medium porosity fritted funnel. The solid residue was washed with DMF (2×0.28 L) and organic fractions combined. The organics were washed with 1 N HCl (1×1.84 L and 1×0.92 L), half-saturated $NaHCO_3$ solution (0.92 L), half-saturated brine (0.92 L), dried over $Na_2SO_4$ and concentrated in vacuo.

The crude product was dissolved in EtOH (142 mL) and TBME (76 mL) and treated with activated charcoal (14 g) at 70° C. for 0.25 hours. The suspension was filtered through Celite. The solution was cooled to 0° C. for 48 hours and the crystals collected (44.88 g). The mother liquor was concentrated and passed over a plug of silica gel eluting with 20% ethyl acetate in hexane yielding an additional 39.25 g of pure product. The total yield of title compound was 84.13 g, (41.4%).

Step 3: 2,3-Dihydro-4-Hydroxybenzofuran

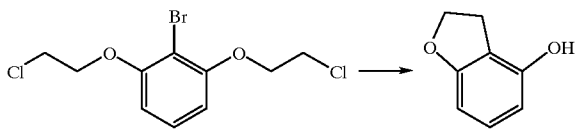

The product of Step 2 (39.25 g) was dissolved in THF (0.5 L) and cooled to −7800. nBuLi (2.5M in hexanes, 300 mL) was then added dropwise over 30 minutes and the reaction stirred at −70° C. for an additional 45 minutes. The solution was then warmed to 0° C. over 10 minutes and stirred at this temperature for 1 hour. Glacial acetic acid (16 mL) was added followed by 1 N NaOH (160 mL) and the layers allowed to separate. The organics were extracted with 1 N NaOH (2×80 mL) and the combined aqueous fractions were then washed with TBME (160 mL).

TBME (240 mL) was then added and the aqueous layer acidified with 6N HCl. The aqueous layer was re-extracted with TBME (240 mL), and the combined organics stirred over activated charcoal (5 g) for 15 minutes, filtered through Celite, and concentrated in vacuo. The crude product was crystallized from toluene and heptane to yield the title compound (16.8 g, 99%).

Step 4: 2,3-Dihydrobenzofuran-4-yl Trifluoromethane Sulfonate

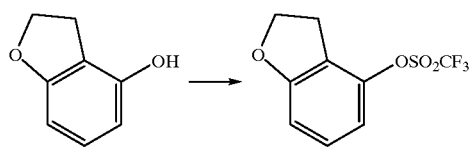

The product of Step 3 (1.0 g) was dissolved in anhydrous dichloromethane (5 mL) and cooled to 0° C. Pyridine (0.87 mL) was then added followed by dropwise addition over 30 minutes of trifluoromethansulfonic anhydide (2.28 g). Stirred from 0° C. to ambient temperature over 1 hour. The methylene chloride solution was then washed with water (2×4.6 mL), 10% phosphoric acid (4.6 mL), saturated NaHCO$_3$ solution (4.6 mL) and brine (2.3 mL). The solution was then treated with activated carbon (170 mg) for 5 minutes, filtered through Celite, dried over Na$_2$SO$_4$ and concentrated in vacuo to yield the title compound (1.74 g, 88%).

2,3-Dihydro-1,4-Benzodioxin-5-yl Trifluoromethane Sulfonate

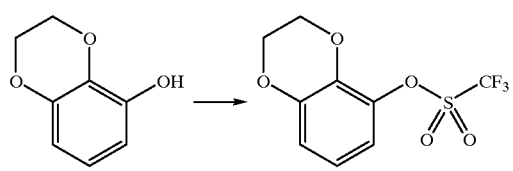

A mixture of 5-hydroxy-2, 3-dihydro-1,4-benzodioxane (prepared according to the procedure of Munk et. al., *J. Med. Chem.*, 40 (1), p. 18–23(1997) (1.81 g, 101.91 mmol) dissolved in CH$_2$Cl$_2$ (20 ml) was cooled to 0° C. Pyridine (1.44 ml, 17.9 mmol) was added and the reaction was stirred for 5 minutes. Trifluoromethanesulphonic anhydride (2.15 ml, 13.1 mmol) was added and the reaction allowed to warm to room temperature and then stirred at room temperature for a total of 6 hours. The organic solution was washed with 10% phosphoric acid (2×15 ml), sodium bicarbonate solution (1×15 ml), and brine (1×15 ml). It was then dried over sodium sulfate and concentrated in vacuo to yield the triflate (2.71 g, 80%) which was used with out further purification.

$^1$H NMR (300 MHz, CDCl$_3$) δ 4.34 (m, 4H), 6.88 (m, 3H).

5-Bromo-2H-2,3-Dihydrobenzopyran

Step 1. 3-Allyloxy Bromobenzene

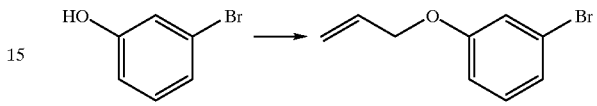

3-Bromophenol (36.3 g, 0.2 mol), allyl bromide (20.7 ml, 0,24so K$_2$CO$_3$ (41.3 g, 0.3 mol) in DMF (100 ml) and THF (100 ml) was stirred at reflux overnight. The reaction mixtures was cooled to room temperature, filtered, and concentrated under reduced pressure to a yellow oil. The product was partitioned between EtOAc and brine, then washed with brine (3×100 ml), dried over MgSO$_4$,and concentrated under reduced pressure to yield the product as a yellow oil. 37.8 g, 890% yield.

$^1$H NMR (CDCl$_3$, 300 MHz): δ 7.18–7.08 (m, 3H), 6.89–6.85 (m, 1 H), 5.45 (dd, J$_1$=1.5 Hz, J$_2$=17.3 Hz, 1H), 5.40 (dd, J$_1$=1.3 Hz, J$_2$=15.7 Hz, 1 H), 4.53 (d, J=2.9 Hz, 2H).

Step 2. 2-Allyl-3-Bromophenol

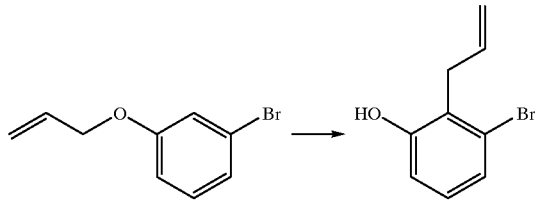

3-Allyloxy bromobenzene (37.85 g, 0.178 mol) was stirred neat at 220° C. until all of the starting material was consumed as indicated by NMR. The crude reaction mixture was purified through silica gel (CH$_2$Cl$_2$) to give 6.0 g of the desired product.

$^1$H NMR (CDCl$_3$, 300 MHz): δ 7.18 (d, J=7.9 Hz, 1H), 6.99 (t, J=8.1 Hz, 1 H), 6.78 (d, J=8.0 Hz, 1 H), 6.05–5.94 (m, 1 H), 5.20–5.09 (m, 2H), 5.08 (s, 1 H), 3.64 (d, J=5.9 Hz, 2H).

Step 3. 2-(3-Hydroxypropyl)-3-Bromophenol

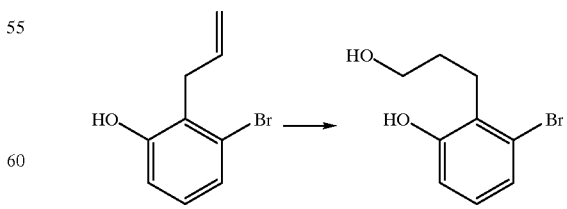

2-Allyl-3-bromophenol (6.0 g, 0.028 mol) dissolved in THF (100 ml) was added dropwise to a solution of BH$_3$.THF (30 ml, 0.03 mol) at 0° C. The resulting mixture was allowed to warm to room temperature and stirred for 1 hour. The reaction was quenched with saturated NaHCO₃ (50 ml) solution and then H₂O₂ (3 ml) was added. The organic layer was separated and the aqueous phase was extracted with EtOAc (3×100 ml). The combined organic layers were washed with brine (1×200 ml), dried over MgSO₄, and concentrated under reduced pressure to provide 7.2 g of the desired product as a yellow oil (quantitative yield).

¹H NMR (CDCl₃, 300 MHz): δ 7.15 (d, J=7.8 Hz, 1H), 6.97 (t, J=7.9 Hz, 1 H), 6.83 (d, J=7.9 Hz, 1 H), 3.65 (t, J=5.7 Hz, 2H), 2.74 (t, J=6.6 Hz, 2H), 1.88–1.83 (m, 2H).

Step 4. 5-Bromo-2H-2,3-Dihydrobenzopyran

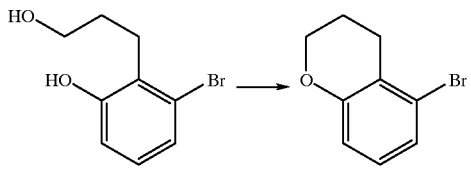

A solution of 2-(3-hydroxypropyl)-3-bromophenol (7.2 g, 0.031 mol) in THF (25 ml) was added dropwise to a mixture of triphenylphosphine (7.2 g, 0.031 mol) and diethyl azodicarboxylate (DEAD) (6.2 ml, 0.04 mol) in THF (75 ml) at 0° C. The resulting mixture was allowed to warm to room temperature, stirred overnight, and concentrated under reduced pressure to give an orange solid. Purification by column chromatography through silica gel (50% EtOAc/hex) provided 6.0 g of the desired product as an orange oil (90% yield).

¹H NMR (CDCl₃, 300 MHz): δ 7.11 (d, J=7.2 Hz, 1 H), 6.96 (t, J=6.3 Hz, 1H), 6.82 (d, J=7.8Hz, 1H), 4.14 (t, J=5.0Hz, 2H), 2.78 (t, J=6.7Hz, 2H), 2.04 (p, J=6.4 Hz, 2H).

2,3-Methylenedioxyphenyl Trifluoromethane Sulfonate

Step 1. 2,3-Methylenedioxyphenol

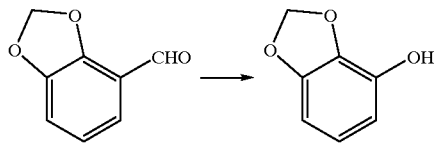

Meta-chloroperoxybenzoic acid (MCPBA) (12.5 g, 0.0726 mol) was added to a solution of 2,3-(methylenedioxy)benzaldehyde (10.0 g, 0.066 mol) in CHCl₃ (200 ml) and the resulting mixture was stirred at room temperature for 2 hours. The reaction mixture was washed with NaHSO₃ (1×200 ml). The organic phase was separated, dried over MgSO₄, and concentrated under reduced pressure to a yellow oil. The oil was dissolved in MeOH (100 ml), one drop of concentrated HCl was added, and the mixture was stirred at room temperature for 1 hour. Solid NaHCO₃ (5 g) was added and the mixture was stirred at room temperature for 1 hour before being filtered and concentrated under reduced pressure to a brown oil. Column chromatography through silica gel (20% EtOAc/hexane) provided the desired product as a white solid (0.6 g, 20% yield).

¹H NMR (CDCl₃, 300 MHz): δ 6.73 (t, J=7.9 Hz, 1 H), 6.51–6.47 (m, 2H), 5.96 (s, 2H), 4.83 (s,1 H).

Step 2. 2,3-Methylenedioxyphenyl Trifluoromethane Sulfonate

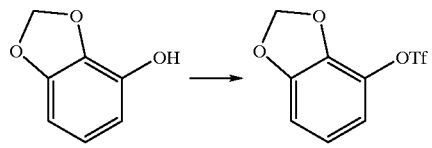

Pyridine (0.69 ml, 0.0086 mol) was added to a solution of 2,3-methylenedioxyphenol (0.6 g, 0.0043 mol) in CH₂Cl₂ (100 ml) at 0° C. and the resulting mixture was stirred at 0° C. for 15 minutes. Triflic anhydride (0.86 ml, 0.0043 mol) was added at 0° C. and the solution was allowed to warm to room temperature and stirred overnight. The crude reaction mixture was partitioned between CH₂Cl₂/sat.Na₂S₂O₅ and the organic phase was washed with water (2x 250 ml), dried over MgSO₄, and concentrated under reduced pressure to give the desired product as a yellow oil (0.9 g, 82% yield).

¹H NMR (CDCl₃, 300 MHz): δ 6.90–6.77 (m, 3H), 6.08 (s, 2H).

Preparation of Intermediates of Formula III (R or S)-N-(2,3-Dihydrobenzfuran-4-yl)-3-(Tert-Butoxycarbonylamino)Pyrrolidine Toluene was degassed with argon for 20 minutes. Palladium acetate (2.16 g, 9.60 mmol) and 2,2'-bis (diphenylphosphino)-1,1'-binaphthyl (BINAP) (9.00 g, 14.45 mmol) were added to the toluene and stirred for 15 minutes. Cesium carbonate (52.16 g, 160.00 mmol) and (R or S)-3-(tert-butoxycarbonylamino)pyrrolidine (17.86 g, 96.02 mmol) were added to the suspension and the color changed to dark red. 3-trifluoromethanesulfoxy-2,3-dihydrobenzfuran (21.44 g, 80.60 mmol) was added and the suspension was heated to reflux for 16 hours. The suspension was cooled, filtered through Celite, and washed with methylene chloride. The solvents were removed by rotary evaporation and the crude product was purified by flash chromatography (25% ethyl acetate/hexanes) to provide 21.1 g of the title compound as a yellow solid (69.51 mmol, 86% yield). LCMS (Purity=100%, MH⁺=305);

¹H NMR (CDCl₃): δ 7.01 (t, J=8.0 Hz, 1H), 6.31 (d, J=7.9 Hz, 1H), 6.14 (d, J=8.1 Hz, 1H),4.79 (bs, 1H), 4.51 (t, J=9.2 Hz, 2H), 4.42 (bs, 1H), 3.65 (m, 2H), 3.38 (m, 5H), 2.25 (m, 1 H) 1.93 (m, 1 H), 1.47 (s, 9H).

(R or S)-N-(2H-2,3-Dihydrobenzopyran-5-yl)-3-(Tert-Butoxycarbonylamino)Pyrrolidine 5-Bromo-2H-2,3-dihydrobenzopyran was used in the coupling procedure described above to give the desired title compound.

¹NMR (CDCl₃, 300 MHz): δ 7.02 (t, J=8.0 Hz, 1 H), 6.50–6.44 (m, 2H), 4.22–4.11 (m, 2H), 3.39–3.34 (m, 2H), 3.04–3.02 (m, 2H), 2.69–2.64 (m, 2H), 2.40–2.15 (m, 1H), 1.97–1.94 (m, 1H), 1.90–1.80 (m, 1H), 1.46 (s, 9H).

(R or S)-N-(2,3-Methylenedioxyphenyl)-3-(Tert-Butoxycarbonylamino)Pyrrolidine 2,3-Methylenedioxyphenyl trifluoromethane sulfonate was used in the coupling procedure described above to give 0.7 g of the desired title compound as a white solid (70% yield). m.p. 71–72° C.;

¹ NMR (CDCl₃, 300 MHz): δ 6.74 (t, J=8.0 Hz, 1 H), 6.35 (d, J=7.8 Hz, 1 H), 6.18 (d, J=8.2 Hz, 1H), 5.85 (s, 2H), 4.90 (s, 1H), 4.30 (s, 1H), 3.63–3.56 (m, 2H), 3.39–3.33 (m, 2H), 2.50–2.20 (m, 1H), 2.00–1.80 (m, 1H), 1.45 (s, 9H). MS (ESI): 307 (M+H)⁺.

(R or S)-N-(2,3-Dihydro-1,4-Benzodioxin-5-yl)-3-(Tert-Butoxycarbonylamino)Pyrrolidine 2,3-Dihydro-1,4-benzodioxin-5-yl trifluoromethane sulfonate was used in the coupling procedure described above to give the desired title compound in 90% yield.

$^1$H NMR (300 MHz, CDCl$_3$) δ 1.45 (s, 9H), 1.8 (m, 1H), 2.26 (m, 1H), 3.2 (m, 2H), 3.5 (m, 2H), 4.26 (m, 5H), 4.81 (broad m, 1 H), 6.31 (dd, J=8.0, J=0.9, 1H), 6.46 (dd, J=8.0, J=0.9, 1H), 6.73 (t, J=8.1, 1H); LRMS (M+H)$^+$=321.16.

Preparation of Intermediates of Formula IV
(R or S)-N-(2,3-Dihydrobenzofuran-4-yl)-3-(Amino)Pyrrolidine Hydrogen chloride was bubbled into dioxane (250 mL) for 30 minutes. This solution was added to solid (R or S)-N-(2,3-dihydrobenzfuran-4-yl)-3-(tert-butoxycarbonylamino)pyrrolidine (11.92 g, 39.21 mmol) and stirred for 1 hour at which time TLC analysis indicated the reaction complete. The solvent was removed by rotary evaporation and the residue taken up in methylene chloride and washed with a solution of 1 N sodium hydroxide. The organic solvent was then removed by rotary evaporation to provide the desired crude amine quantitatively.

$^1$H NMR (300 MHz, CDCl$_3$) 66.98 (1H, t, J=8.0 Hz), 6.26 (1H, d, J=7.8 Hz), 6.11 (1H, d, J=8.2Hz), 4.48 (2H, t, J=8.6Hz), 3.69–3.51 (3H, m), 3.48–3.30 (3H, m), 3.20–3.10 (1H, m), 2.22–2.10 (1H, m), 1.81–1.66 (3H, m);

$^{13}$C NMR (75 MHz, CDCl$_3$) δ 161.6, 146.6, 128.9, 110.4, 105.9, 99.8, 70.6, 58.1, 51.4, 47.9, 34.9, 31.0;

LCMS (100%); LRMS (M+H)+205.25.

(R or S)-N-(2H-2,3-Dihydrobenzopyran-5-yl)-3-(Amino)Pyrrolidine (R or S)-N-(2H-2,3-Dihydrobenzopyran-5-yl)-3-(tert-butoxycarbonylamino)pyrrolidine was used in the deprotection procedure described above to give the desired title compound.

$^1$H NMR (CDCl$_3$, 300 MHz): δ 7.01 (t, J=8.0 Hz, 1 H), 6.47–6.44 (m, 2H), 4.18 (t, J=5.1 Hz, 2H), 3.63–3.60 (m, 1H), 3.38–3.30 (m, 2H), 3.20–3.15 (m, 1 H), 2.98–2.95 (m, 1 H), 2.67 (t, J=6.2 Hz, 2H), 2.25–2.21 (m, 1 H), 1.98–1.96 (m, 2H), 1.72–1.70 (m, 1H); MS (ESI): 219.

(R or S)-N-(2,3-Methylenedioxyphenyl)-3-(Amino)Pyrrolidine (R or S)-N-(2,3-Methylenedioxyphenyl)-3-(tert-butoxycarbonylamino)pyrrolidine was used in the deprotection procedure described above to give 0.3 g of the desired title compound as a yellow oil (67% yield).

$^1$H NMR (CDCl$_3$, 300 MHz): δ 6.74 (t, J=8.0 Hz, 1H), 6.33 (d, J=7.8 Hz, 1H), 6.18 (d, J=8.3 Hz, 1H), 5.84 (s, 2H), 3.71–3.55 (m, 3H), 3.47–3.39 (m, 1H), 3.22–3.15 (m, 1H), 2.24–2.13 (m, 1H), 1.78–1.72 (m, 1H); MS (ESI): 207.

(R or S)-N-(2,3-Dihydro-1.4-Benzodioxin-5-yl)-3-(Amino)Pyrrolidine (R or S)-N-(2,3-Dihydro-1,4-benzodioxin-5-yl)-3-(tert-butoxycarbonylamino)pyrrolidine was used in the deprotection procedure described above to give the desired title compound in 95% crude yield.

$^1$H NMR (300 MHz, CDCl$_3$) 61.72 (m, 1H), 1.91 (broad s, 2H), 2.18 (m, 1 H), 3.09 (m, 1 H), 3.35 (m, 1 H), 3.51 (m, 2H), 3.63 (m, 1 H), 4.28 (m, 4H), 6.33 (dd, J=8.0, J=1.4, 1H), 6.43 (dd, J=8.0, J=1.4, 1H), 6.73 (t, J=8.1, 1H).

General Procedure for the Preparation of Compounds of Formula I

EXAMPLE 1

(S)-N-[N-(2,3-Dihydrobenzofuran-4-yl)-Pyrrolidin-3-yl]Acetamide (S)-N-(2,3-dihydrobenzofuran-4-yl)-3-(amino)pyrrolidine (0.1 mmol) and triethylamine (0.15 mmol) were dissolved in CH$_2$Cl$_2$. Acetylchloride (0.12 mmol) was added, and the reaction was stirred at room temperature for 16 hours. The organics were then washed with 1 N HCl, NaHCO$_3$, and brine. The organic solution was dried over sodium sulfate, concentrated in vacuo, and purified by silica gel column chromatography eluting with 4% methanol in CH$_2$Cl$_2$ to yield the title compound.

IR (neat) υ 3240, 3072, 2968, 2852, 1639, 1549,1454,1375,1233, 758 cm$^{-1}$;

$^1$H NMR (300 MHz, CDCl$_3$) 86.99 (1H, t, J=8.0Hz), 6.27 (1H, d, J=7.8 Hz), 6.12 (1H, d, J=8.2Hz), 5.28 (1H, br), 4.58–4.52 (1H, m), 4.52–4.42 (2H, m), 3.65–3.50 (2H, m), 3.42–3.24 (4H, m), 2.29–2.10 (1H, m), 1.97 (3H, s), 1.97–1.86 (1 H, m);

$^{13}$C NMR (75 MHz, CDCl$_3$): 3170.0, 161.6,146.1, 129.1, 111.0, 106.2, 100.5, 70.6, 55.4, 49.4, 47.6, 31.7, 30.9, 23.5;

LCMS (100%); LRMS (M+H)$^+$247.18;

Anal. Calcd for C$_{14}$H$_{18}$N$_2$O$_2$: C, 68.27; H, 7.37; N, 11.37. Found: C, 67.91; H, 7.40; N, 10.96.

[α]$_D$$^{25}$–51 (c, 0.29, MeOH).

The following examples 2–17 were prepared using the appropriate amino pyrrolidine and acid chloride according to the general procedure described in Example 1.

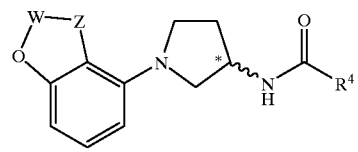

| Example No. | R$^4$ | Z | W | Enantiomer (*) | [α]$_D$$^{25}$ (c, MeOH) | $^1$H NMR (300 MHz, CDCl$_3$) δ (mp) |
|---|---|---|---|---|---|---|
| 2 | Me | CH$_2$ | CH$_2$ | R | +50 (0.11) | 6.99 (1H, t, J=8.0 Hz), 6.27 (1H, d, J=7.8 Hz), 6.12 (1H, d, J= 8.2 Hz), 5.28 (1H, br), 4.58–4.52 (1H, m), 4.52–4.42 (2H, m), 3.65–3.50 (2H, m), 3.42–3.24 (4H, m), 2.29–2.10 (1H, m), 1.97 (3H, s), 1.97–1.86 (1H, m). |
| 3 | Et | CH$_2$ | CH$_2$ | S | –53 (0.26) | 6.99 (1H, t, J=8.0 Hz), 6.29 (1H, d, J=7.8 Hz), 6.12 (1H, d, J= 8.2 Hz), 5.87–5.76 (1H, br), 4.60–4.50 (1H, m), 4.50–4.42 |
| 4 | Et | CH$_2$ | CH$_2$ | R | +52 (0.32) | (2H, m), 3.67–3.50 (2H, m), 3.42–3.23 (4H, m), 2.30–2.15 (3H, m), 1.96–1.85 (1H, m), 1.19–1.07 (3H, m). |

-continued

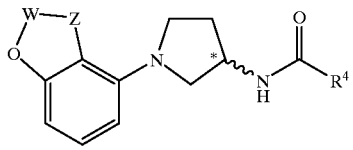

| Example No. | R⁴ | Z | W | Enantiomer (*) | $[\alpha]_D^{25}$ (c, MeOH) | ¹H NMR (300 MHz, CDCl₃) δ (mp) |
|---|---|---|---|---|---|---|
| 5 | nPr | CH₂ | CH₂ | S | −21 (0.29) | 6.99 (1H, t, J=8.0 Hz), 6.29 (1H, d, J=7.8 Hz), 6.12 (1H, d, J= 8.2 Hz), 5.80–5.76 (1H, br), 4.62–4.52 (1H, m), 4.52–4.42 |
| 6 | nPr | CH₂ | CH₂ | R | +41 (0.25) | (2H, m), 3.65–3.50 (2H, m), 3.42–3.24 (4H, m), 2.30–2.18 (1H, m), 2.13 (2H, t, J=7.5 Hz), 1.96–1.84 (1H, m), 1.72– 1.56 (2H, m), 1.00–0.88 (3H, m). |
| 7 | iPr | CH₂ | CH₂ | S | −50 (0.34) | 6.99 (1H, t, J=8.0 Hz), 6.29 (1H, d, J=7.8 Hz), 6.12 (1H, d, J= 8.2 Hz, 5.80–5.76 (1H, br), 4.62–4.50 (1H, m), 4.50–4.40 |
| 8 | iPr | CH₂ | CH₂ | R | +47 (0.26) | (2H, m), 3.68–3.50 (2H, m), 3.44–3.20 (4H, m), 2.40–2.18 (2H, m), 1.95–1.82 (1H, m), 1.19–1.12 (6H, m). |
| 9 | cPr | CH₂ | CH₂ | S | −51 (0.30) | 6.99 (1H, t, J=8.0 Hz), 6.29 (1H, d, J=7.8 Hz), 6.12(1H, d, J= 8.2 Hz), 6.02–5.96 (1H, br), 4.62–4.52 (1H, m), 4.52–4.42 |
| 10 | cPr | CH₂ | CH₂ | R | +48 (0.21) | (2H, m), 3.67–3.51 (2H, m), 3.42–3.24 (4H, m), 2.30–2.16 (1H, m), 1.98–1.87 (1H, m), 1.38–1.26 (1H, m). 1.00–0.94 (2H, m), 0.78–0.68 (2H, m). |
| 11 | CH₂OMe | CH₂ | CH₂ | S | −40 (0.27) | 7.00 (1H, t, J=7.7 Hz), 6.72–6.66 (1H, br), 6.30 (1H, d, J= 7.8 Hz), 6.13 (1H, d, J=8.2 Hz), 4.64–4.56 (1H, m), 4.54– 4.44 (2H, m), 3.88 (2H, d, J=1.4 Hz), 3.70–3.51 (2H, m), 3.40 (3H, s), 3.47–3.27 (4H, m), 2.34–2.20 (1H, m), 1.99–1.86 (1H, m). |
| 12 | Et | O | CH₂ | R | — | 6.75 (t, J=8.0 Hz, 1H), 6.36 (d, J=7.0 Hz, 1H), 6.20 (d, J=8.8 Hz, 1H), 5.85 (s, 2H), 4.50–4.40 (m, 2H), 4.30–4.15 (m, 1H), 3.61–3.55 (m, 2H), 3.39–3.33 (m, 2H), 3.26–3.17 (m, 2H), 2.28– 2.23 (m, 1H), 1.90–1.86 (m, 1H), 1.14 (t, J=7.2 Hz, 3H). (mp = 156–157° C.) |
| 13 | Et | CH₂ | (CH₂)₂ | S | — | 7.03 (t, J=8.1 Hz, 1H), 6.51–6.45 (m, 2H), 5.74 (s, 1H), 4.23– 4.15 (m, 2H), 3.44–3.35 (m, 2H), 3.06–3.01 (m, 1H), 2.67 (t, J= 6.1 Hz, 2H), 2.34–2.31 (m, 1H), 2.21 (q, J=7.5 Hz, 2H), 1.99– 1.95 (m, 2H), 1.94–1.90 (m, 1H), 1.19 (t, J=7.5 Hz, 3H). |
| 14 | Me | O | (CH₂)₂ | S | — | 1.90 (m, 1H), 2.0 (s, 3H), 2.31 (m, 1H), 3.17 (m, 1H), 3.35 (m, 1H), 3.46 (m, 1H), 3.61 (m, 1H), 4.29 (m, 4H), 4.59 (m, 1H), 6.35 (m, 1H), 6.51 (m, 1H), 6.76 (t, J=8.2, 1H). |
| 15 | Et | O | (CH₂)₂ | S | — | 1.16 (t, J=7.6, 3H) 1.86 (m, 1H), 2.2 (q, J=7.6, 2H), 2.31 (m, 1H), 3.17 (m, 1H), 3.31 (m, 1H), 3.45 (m, 1H), 3.59 (m, 1H), 4.29 (m, 4H), 4.6 (m, 1H), 4.79 (broad s, 1H), 6.38 (m, 1H), 6.5 (d, J=8.0, 1H), 6.75 (t, J=8.2, 1H). |
| 16 | nPr | O | (CH₂)₂ | S | — | 0.96 (t, J=7.4, 3H), 1.69 (m, 2H), 1.85 (m, 1H), 2.15 (t, J= 7.2, 2H), 2.3 (m, 1H), 3.16 (m, 1H), 3.31 (m, 1H), 3.43 (m, 1H), 3.58 (m, 1H), 4.28 (m, 4H), 4.6 (m, 1H), 5.78 (broad m, 1H), 6.38 (m, 1H), 6.50 (d, J=8.1, 1H), 6.75 (t, J=8.1, 1H). |
| 17 | cPr | O | (CH₂)₂ | S | — | 0.74 (m, 2H), 0.98 (m, 2H), 1.33 (m, 1H), 1.9 (m, 1H), 2.3 (m, 1H), 3.18 (m, 1H), 3.35 (m, 1H), 3.47 (m, 1H), 3.62 (m, 1H), 4.3 (m, 4H), 4.62 (m, 1H), 6.06 (broad m, 1H), 6.42 (m, 1H), 6.51 (d, J=8.0, 1H), 6.76 (t, J=8.2, 1H). |

EXAMPLE 18
(R)-N-[N-(2,3-Dihydrobenzofuran-4-yl)-Pyrrolidin-3-yl]-N'-Methyl Urea (R)-N-(2,3-Dihydrobenzofuran-4-yl)-3-(amino) pyrrolidine (0.1 mmol) was dissolved in CH₂Cl₂ and methyl isocyanate (0.12 mmol) was added. The reaction was stirred at room temperature for 1 hour. The solvents were removed in vacuo, and the compound purified by flash chromatography eluting with 10% methanol in ethyl acetate to give 130 mg (98%) of the desired product as a solid.

IR (film, cm⁻¹) 3313 (br), 1628;

¹H NMR (300 MHz, CDCl₃): δ 6.97 (t, J=8.1 Hz, 1 H), 6.29 (d, J=7.8 Hz, 1 H), 6.11 (d, J=8.1 Hz, 1 H), 4.52–4.36 (m, 3 H), 3.62–3.19 (m, 6 H), 2.78 (s, 3 H), 2.23–2.14 (m, 1 H), 1.97–1.82 (m, 1 H);

¹³C NMR (75 MHz, CDCl₃): 6161.5,158.3,146.3, 129.0, 110.8,106.0, 100.2, 70.5, 55.9, 50.1, 47.6, 32.1, 30.9, 27.3;

$[\alpha]_D^{25}$ +22.7 (c, 0.12, MeOH); MS(ESI) 262 (M+H)⁺;

Anal Calcd for C₁₄H₁₉N₃O₂: C, 64.35; H, 7.33. Found: C, 64.60; H, 7.20.

The following examples 19–29 were prepared using the appropriate amino pyrrolidine and isocyanate according to the general procedure described in Example 18.

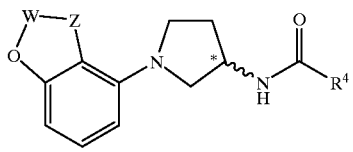

| Example No. | R⁴ | Z | W | Enantiomer (*) | $[\alpha]_D^{25}$ (c, MeOH) | ¹H NMR (300 MHz, CDCl₃) δ (mp) |
|---|---|---|---|---|---|---|
| 19 | NHMe | CH₂ | CH₂ | S | −21 (0.29) | 6.97 (t, J=8.1 Hz, 1H), 6.29 (d, J=7.8 Hz, 1H), 6.11 (d, J=8.1 Hz, 1H), 4.52–4.36 (m, 3 H), 3.62–3.19 (m, 6H), 2.78 (s, 3H), 2.23–2.14 (m, 1H), 1.97–1.82 (m, 1H). |
| 20 | NHEt | CH₂ | CH₂ | S | −20 (0.32) | 7.01 (t, J=8.0 Hz, 1H), 6.32 (d, J=7.9 Hz, 1H), 6.16 (d, J=8.1 Hz, 1H), 4.68 (bs, 1H), 4.50 (t, J=9.2 Hz, 3H), 4.35 (bs, 1H), 3.62 (m, 2H), 3.36 (m, 4H), 3.21 (m, 2H), 2.25 (m, 1H) 1.93 (m, 1H), 1.13 (t, J=7.2 Hz, 3H). |
| 21 | NHEt | CH₂ | CH₂ | R | +17 (0.25) | (mp = 143–145° C.) |
| 22 | NHnPr | CH₂ | CH₂ | S | −17 (0.28) | 6.97 (t, J=8.1 Hz, 1H), 6.25 (d, J=7.8 Hz, 1H), 6.07 (d, J=8.1 Hz, 1H), 5.35 (d, J=7.4 Hz, 1H), 5.07 (t, J=5.5 Hz, 1H), |
| 23 | NHnPr | CH₂ | CH₂ | R | +16 (0.10) | 4.47–4.29 (m, 3H), 3.60–3.04 (m, 8H), 2.78 (s, 3H), 2.21–2.07 (m, 1H), 1.86–1.76 (m, 1H), 1.46 (m, 2H), 0.88 (t, J=7.1 Hz, 3H). |
| 24 | NHMe | O | CH₂ | R | — | 6.75 (t, J=8.0 Hz, 1H), 6.36 (d, J=7.8 Hz, 1H), 6.20 (d, J=8.2 Hz, 1H), 5.85 (s, 2H), 4.46–4.43 (m, 2H), 4.22–4.21 (m, 1H), 3.63–3.55 (m, 2H), 3.40–3.31 (m, 2H), 2.78 (d, J=4.9 Hz, 3H), 2.30–2.23 (m, 1H), 1.91–1.89 (m, 1H). |
| 25 | NHEt | O | CH₂ | R | — | 6.75 (t, J=8.0 Hz, 1H), 6.36 (d, J=7.0 Hz, 1H), 6.20 (d, J=8.8 Hz, 1H), 5.85 (s, 2H), 4.50–4.40 (m, 2H), 4.30–4.15 (m, 1H), 3.61–3.55 (m, 2H), 3.39–3.33 (m, 2H), 3.26–3.17 (m, 2H), 2.28–2.23 (m, 1H), 1.90–1.86 (m, 1H), 1.14 (t, J=7.2 Hz, 3H). |
| 26 | NHEt | CH₂ | (CH₂)₂ | S | — | 7.01 (t, J=8.9 MHz, 1H), 6.49–6.43 (m, 2H), 4.45–4.43 (m, 2H), 4.21–4.13 (m, 3H), 3.31–3.25 (m, 2H), 3.22–3.18 (m, 2H), 3.05–3.01 (m, 2H), 2.65 (t, J=6.3 Hz, 2H), 2.40–2.30 (m, 1H), 2.05–1.93 (m, 2H), 1.90–1.80 (m, 1H), 1.30 (t, J=7.2 Hz, 3H). |
| 27 | NHMe | O | (CH₂)₂ | S | — | 1.87 (m, 1H), 2.28 (m, 1H), 2.76 (d, J=4.8, 3H), 3.16 (m, 1H), 3.28 (m, 1H), 3.46 (m, 1H), 3.55 (m, 1H), 4.25 (m, 4H), 4.41 (m, 1H), 4.61 (broad d, J=4.4, 1H), 4.89 (broad d, J=7.1, 1H), 6.36 (m, 1H), 6.48 (dd, J=8.2, J=1.4, 1H), 6.74 (t, J=8.2, 1H). |
| 28 | NHEt | O | (CH₂)₂ | S | — | 1.13 (t, J=7.2, 3H) 1.92 (m, 1H), 2.33 (m, 1H), 3.22 (m, 3H), 3.33 (m, 1H), 3.49 (m, 1H), 3.62 (m, 1H), 4.30 (m, 4H), 4.43 (m, 1H), 4.95 (broad s, 1H), 6.54 (m, 2H), 6.77 (t, J=8.2, 1H). |
| 29 | NHnPr | O | (CH₂)₂ | S | — | 0.91 (t, J=7.4, 3H), 1.5 (m, 2H), 1.85 (m, 1H), 2.28 (m, 1H), 3.12 (m, 3H), 3.28 (m, 1H), 3.45 (m, 1H), 3.55 (m, 1H), 4.26 (m, 4H), 4.4 (m, 1H), 4.58 (broad m, 1H), 4.82 (broad d, J=6.6, 1H), 6.37(d, J=8.0, 1H), 6.48(dd, J=8.1, J=1.4, 1H), 6.74 (t, J=8.1, 1H) |

EXAMPLE 30
(R)-N-[N-(2,3-Dihydrobenzofuran-4-yl)-Pyrrolidin-3-yl]-N'-Cylopropyl Urea Phosgene (1 mL, 20% in toluene) was added to a solution of (R)-N-(2,3-dihydrobenzofuran-4-yl)-3-(amino)pyrrolidine (102 mg) and pyridine (79 mg) in THF (5.6 mL) at 0° C. After stirring for 20 min, cyclopropylamine (228 mg) was added to the reaction and the reaction mixture was allowed to warm to room temperature. After stirring for 2 h, the reaction was quenched with water and THF was removed. The residue was purified by flash chromatography over silica gel (elution with 5% methanol in ethyl acetate) to give 110 mg (77%) of the desired product as solid.

IR (film, cm⁻¹) 3319 (br), 1631;

¹H NMR (300 MHz, CDCl₃): δ 6.96 (t, J=8.1 Hz, 1 H), 6.25 (d, J=7.8 Hz, 1 H), 6.09 (d, J=8.1 Hz, 1 H), 5.1 (d, J=7.3 Hz, 1 H), 4.68 (br s, 1 H), 4.46–4.38 (m, 3 H), 3.64–3.33 (m, 6 H), 2.38–2.14 (m, 2 H), 1.89–1.82 (m, 1 H), 1.97–1.87 (m, 1 H), 0.71–0.63 (m, 2 H), 0.51–0.45 (m, 2 H);

$[\alpha]_D^{25}$ +8.7 (c, 0.1, MeOH); MS(ESI) 288 (M+H)⁺;

Anal Calcd for C₁₆H₂₁N₃O₂: C, 66.88; H, 7.37. Found: C, 67.13; H, 7.68.

The following examples 31–33 were prepared using the appropriate acid chloride according to the general procedure described in Example 30.

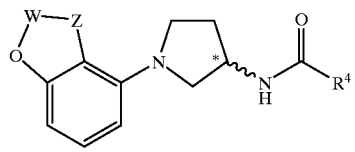

| Example No. | R⁴ | Z | W | Enantiomer (*) | $[\alpha]_D^{25}$ (c, MeOH) | ¹H NMR (300 MHz, CDCl₃) δ (mp) |
|---|---|---|---|---|---|---|
| 31 | NHcPr | CH₂ | CH₂ | S | −4.3 (0.32) | 6.96 (t, J=8.1 Hz), 6.25 (d, J=7.8 Hz, 1H), 6.09 (d, J= 8.1 Hz, 1H), 5.1 (d, J=7.3 Hz, 1H), 4.68 (br s, 1H), 4.46–4.38 (m, 3H), 3.64–3.33 (m, 6H), 2.38–2.14 (m, 2H), 1.89–1.82 (m, 1H), 1.97–1.87 (m,.1H), 0.71–0.63 (m, 2H), 0.51–0.45 (m, 2H) |
| 32 | NMe₂ | CH₂ | CH₂ | S | +18 (0.30) | |
| 33 | NMe₂ | CH₂ | CH₂ | R | | |

EXAMPLE 34
(S)-N-[N-(5-Chloro-2,3-Dihydrobenzofuran-4-yl)-Pyrrolidin-3-yl]Acetamide (S)-N-(2,3-Dihydrobenzofuran-4-yl)-3-(amino)pyrrolidine (0.1 mmol) and N-chlorosuccinimide (0.11 mmol) were dissolved in acetonitrile (5 ml) and heated to reflux for 16 hours. The reaction was cooled and the solvent removed in vacuo. The crude product was purified by preparative HPLC and the major product of the reaction yielded the title compound.

¹H NMR (300 MHz, CDCl₃): δ 1.89 (m, 1 H), 2.0 (s, 3H), 2.3 (m, 1 H), 3.22 (m, 6H), 3.48 (m, 1 H), 3.58 (m, 1 H), 4.58 (m, 3H), 5.96 (broad m, 1 H), 6.49 (d, J=8.4, 1H), 7.10 (d, J=8.4, 1H); LRMS M+H=281.16; analytical HPLC purity=97%.

EXAMPLE 35
(S)-N-[N-(5,7-Dichloro-2,3-Dihydrobenzofuran-4-yl)-Pyrrolidin-3-yl]Acetamide The crude product isolated in Example 34 from the reaction of (S)-N-(2,3-dihydrobenzofuran-4-yl)-3-(amino)pyrrolidine (0.1 mmol) and N-chlorosuccinimide (0.11 mmol) was purified by preparative HPLC and the minor product of the reaction was isolated to yield the title compound.

¹H NMR (300 MHz, CDCl₃): 61.85 (m, 1H), 2.0 (s, 3H), 2.3 (m, 1H), 3.18 (m, 2H), 3.36 (t, J=8.76, 2H), 3.46 (m, 1 H), 3.56 (m, 1 H), 4.57 (m, 1 H), 4.67 (t, J=8.76, 2H), 5.90 (broad m, 1H), 7.16 (s, 1H); LRMS M+H=315.09, 317.08; analytical HPLC purity=97%.

The following examples 36–43 were prepared using the appropriate amino pyrrolidine according to the general procedure described in Examples 34 and 35.

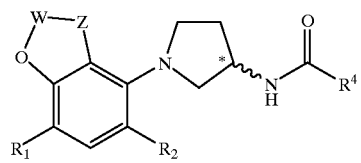

| Example No. | R¹ | R² | R⁴ | Z | W | Enantiomer (*) | $[\alpha]_D^{25}$ (c, MeOH) | ¹H NMR(300 MHz, CDCl₃) δ (mp) |
|---|---|---|---|---|---|---|---|---|
| 36 | H | Cl | nPr | CH₂ | CH₂ | S | | 0.97 (t, J=7.4, 3H), 1.68 (m, 2H), 1.88 (m, 1H), 2.17 (t, J=7.23, 2H), 2.3 (m, 1H), 3.23 (m, 4H), 3.47 (m, 1H), 3.59 (m, 1H), 4.57 (m, 3H), 5.96 (broad d, J=7.0, 1H), 6.49 (d, J=8.4, 1H), 7.10(d, J=8.4, 1H). |
| 37 | Cl | Cl | nPr | CH₂ | CH₂ | S | | 0.97 (t, J=7.4, 3H), 1.68 (m, 2H), 1.85 (m, 1H), 2.17 (t, J=7.23, 2H), 2.3 (m, 1H), 3.18 (m, 2H), 3.36 (t, J=8.73, 2H), 3.46 (m, 1H), 3.56 (m, 1H), 4.58 (m, 1H), 4.66 (t, J=8.73, 2H), 5.90 (broad d, J=7.2, 1H), 7.16 (s, 1H). |
| 38 | H | Cl | cPr | CH₂ | CH₂ | S | | 7.11 (d, J=8.4 Hz, 1H), 6.50 (d, J=8.4 Hz, 1H), 6.16 (s, 1H), 4.59 (t, J=8.6 Hz, 2H), 3.63 (s, 1H), 3.53–3.49 (m, 1H), 3.27 (t, J=10.6 Hz, 2H), 2.35–2.30 (m, 1H), 1.92–1.88 (m, 1H), 1.66–1.62 (m, 2H), 1.44–1.41 (m, 1H), 1.00–0.97 (m, 2H), 0.88–0.77 (m, 2H). |

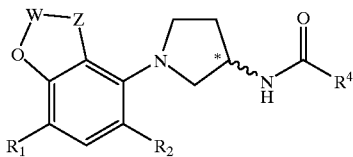

| Example No. | R¹ | R² | R⁴ | Z | W | Enantiomer (*) | $[\alpha]_D^{25}$ (c, MeOH) | ¹H NMR(300 MHz, CDCl₃) δ (mp) |
|---|---|---|---|---|---|---|---|---|
| 39 | Cl | Cl | cPr | CH₂ | CH₂ | S | | 7.15 (m, 1H), 6.11 (m, 1H), 4.65 (t, J=8.7 Hz, 2H), 3.59–3.53 (m, 1H), 3.49–3.46 (m, 2H), 3.36 (t, J=8.8 Hz, 2H), 3.22–3.18 (m, 2H), 2.31–2.28 (m, 1H), 1.90–1.80 (m, 1H), 1.36–1.31 (m, 1H), 0.99–0.95 (m, 2H), 0.78–0.73 (m, 2H). |
| 40 | H | Cl | NHEt | CH₂ | CH₂ | S | | 7.26 (d, J=8.6 Hz, 1H), 6.75 (d, J–8.6 Hz, 1H), 4.67 (t, J=7.1 Hz, 2H), 4.17–4.03 (m, 2H), 3.96–3.76 (m, 4H), 3.20 (q, J=7.1 Hz, 2H), 2.64 (s, 1H), 2.26 (s, 1H), 1.18 (t, J=7.1 Hz, 3H). |
| 41 | H | Cl | NHEt | CH₂ | CH₂ | R | | |
| 42 | Cl | Cl | NHEt | CH₂ | CH₂ | S | | 7.26 (s, 1H), 6.23 (s, 1H), 4.70 (t, J=7.9 Hz, 2H), 4.46 (s, 1H), 3.72–3.64 (m, 2H), 3.50–3.46 (m, 2H), 3.35–3.33 (m, 2H), 3.18 (q, J=6.5 Hz, 2H), 2.43 (m, 1H), 2.05 (m, 1H), 1.96 (t, J=7.0 Hz, 3H). |
| 43 | Cl | Cl | NHEt | CH₂ | CH₂ | R | | |

We claim:

1. A compound of the formula

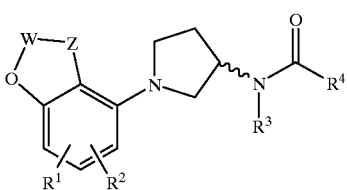

wherein
the wavy bond ∼∼∼ represents the racemate, the (R)-enantiomer or the (S)-enantiomer;
$R^1$ and $R^2$ each are independently hydrogen or halogen;
W is $CR^5$, $CR^5R^6$ or $(CH_2)n$, with n=1–2;
Z is $CH_2$, CH or oxygen;
$R^3$ is hydrogen or $C_{1-4}$ alkyl;
$R^4$ is $C_{1-6}$ alkyl, $C_{3-6}$ cycloalkyl, $C_{1-3}$ haloalkyl, $C_{2-6}$ alkenyl, $C_{1-6}$ alkyamino, $C_{3-6}$ cycloalkylamino, di($C_{1-4}$)alkylamino, $C_{1-4}$ alkoxy ($C_{1-4}$)alkyl, $C_{1-4}$ alkylthio ($C_{1-4}$)alkyl or $C_{1-4}$ trifluoromethyl($C_{1-2}$)alkyl; and
$R^5$ and $R^6$ each are independently hydrogen or $C_{1-4}$ alkyl;
or a nontoxic pharmaceutically acceptable salt, hydrate or solvate thereof.

2. The compound of claim 1 wherein the wavy bond ∼∼∼ represents the (R)-enantiomer or a nontoxic pharmaceutically acceptable salt, hydrate or solvate thereof.

3. The compound of claim 1 wherein the wavy bond ∼∼∼ represents the (S)-enantiomer or a nontoxic pharmaceutically acceptable salt, hydrate or solvate thereof.

4. The compound of claim 1 wherein $R^3$, $R^5$, and $R^6$ are hydrogen or a nontoxic pharmaceutically acceptable salt, hydrate or solvate thereof.

5. The compound of claim 4 wherein R4 is $C_{1-6}$ alkyl, $C_{3-6}$ cycloalkyl, $C_{1-6}$ alkyamino, $C_{3-6}$ cycloalkylamino, $C_{14}$ alkoxy($C_{1-4}$)alkyl or a nontoxic pharmaceutically acceptable salt, hydrate or solvate thereof.

6. The compound of claim 1 wherein W is CH, $CH_2$ or $(CH_2)_2$ and Z is CH or $CH_2$ or a nontoxic pharmaceutically acceptable salt, hydrate or solvate thereof.

7. The compound of claim 6 selected from the group consisting of:
(S)-N-[N-(2,3-dihydrobenzofuran-4-yl)-pyrrolidin-3-yl] acetamide;
(R)-N-[N-(2,3-dihydrobenzofuran-4-yl)-pyrrolidin-3-yl] acetamide;
(S)-N-[N-(2,3-dihydrobenzofuran-4-yl)-pyrrolidin-3-yl] propanamide;
(R)-N-[N-(2,3-dihydrobenzofuran-4-yl)-pyrrolidin-3-yl] propanamide;
(S)-N-[N-(2,3-dihydrobenzofuran-4-yl)-pyrrolidin-3-yl] butyramide;
(R)-N-[N-(2,3-dihydrobenzofuran-4-yl)-pyrrolidin-3-yl] butyramide;
(S)-N-[N-(2,3-dihydrobenzofuran-4-yl)-pyrrolidin-3-yl] isobutyramide;
(R)-N-[N-(2,3-dihydrobenzofuran-4-yl)-pyrrolidin-3-yl] isobutyramide;
(S)-N-[N-(2,3-dihydrobenzofuran-4-yl)-pyrrolidin-3-yl] cyclopropane carboxamide;
(R)-N-[N-(2,3-dihydrobenzofuran-4-yl)-pyrrolidin-3-yl] cyclopropane carboxamide;
(S)-N-[N-(2,3-dihydrobenzofuran-4-yl)-pyrrolidin-3-yl] methoxyacetamide;
(S)-N-[N-(2H-2,3-dihydrobenzopyran-5-yl)-pyrrolidin-3-yl]propanamide;
(R)-N-[N-(2,3-dihydrobenzofuran-4-yl)-pyrrolidin-3-yl]-N'-methyl urea;
(S)-N-[N-(2,3-dihydrobenzofuran-4-yl)-pyrrolidin-3-yl]-N'-methyl urea;
(S)-N-[N-(2,3-dihydrobenzofuran-4-yl)-pyrrolidin-3-yl]-N'-ethyl urea;
(R)-N-[N-(2,3-dihydrobenzofuran-4-yl)-pyrrolidin-3-yl]-N'-ethyl urea;

(S)-N-[N-(2,3-dihydrobenzofuran-4-yl)-pyrrolidin-3-yl]-N'-n-propyl urea;

(R)-N-[N-(2,3-dihydrobenzofuran-4-yl)-pyrrolidin-3-yl]-N'-n-propyl urea;

(S)-N-[N-(2H-2,3-dihydrobenzopyran-5-yl)-pyrrolidin-3-yl]-N'-ethyl urea;

(R)-N-[N-(2,3-dihydrobenzofuran-4-yl)-pyrrolidin-3-yl]-N'-cylopropyl urea;

(S)-N-[N-(2,3-dihydrobenzofuran-4-yl)-pyrrolidin-3-yl]-N'-cylopropyl urea;

(S)-N-[N-(2,3-dihydrobenzofuran-4-yl)-pyrrolidin-3-yl]-N',N'-dimethyl urea;

(R)-N-[N-(2,3-dihydrobenzofuran-4-yl)-pyrrolidin-3-yl]-N',N'-dimethyl urea;

(S)-N-[N-(5-chloro-2,3-dihydrobenzofuran-4-yl)-pyrrolidin-3-yl]acetamide;

(S)-N-[N-(5,7-dichloro-2,3-dihydrobenzofuran-4-yl)-pyrrolidin-3-yl]-acetamide;

(S)-N-[N-(5-chloro-2,3-dihydrobenzofuran-4-yl)-pyrrolidin-3-yl]butyramide;

(S)-N-[N-(5,7-dichloro-2,3-dihydrobenzofuran-4-yl)-pyrrolidin-3-yl]-butyramide;

(S)-N-[N-(5-chloro-2,3-dihydrobenzofuran-4-yl)-pyrrolidin-3-yl]-cyclopropane carboxamide;

(S)-N-[N-(5,7-dichloro-2,3-dihydrobenzofuran-4-yl)-pyrrolidin-3-yl]-cyclopropane carboxamide;

(S)-N-[N-(5-chloro-2,3-dihydrobenzofuran-4-yl)-pyrrolidin-3-yl]-N'-ethyl urea;

(R)-N-[N-(5-chloro-2,3-dihydrobenzofuran-4-yl)-pyrrolidin-3-yl]-N'-ethyl urea;

(S)-N-[N-(5,7-dichloro-2,3-dihydrobenzofuran-4-yl)-pyrrolidin-3-yl]-N'-ethyl urea; and (R)-N-[N-(5,7-dichloro-2,3-dihydrobenzofuran-4-yl)-pyrrolidin-3-yl]-N'-ethyl urea;

or a nontoxic pharmaceutically acceptable salt, hydrate or solvate thereof.

8. The compound of claim 1 wherein W is $CH_2$ or $(CH_2)_2$ and Z is oxygen or a nontoxic pharmaceutically acceptable salt, hydrate or solvate thereof.

9. The compound of claim 8 selected from the group consisting of:

(R)-N-[N-(2,3-methylenedioxyphen-1-yl)-pyrrolidin-3-yl]propanamide;

(S)-N-[N-(2,3-dihydro-1,4-benzodioxin-5-yl)-pyrrolidin-3-yl]acetamide;

(S)-N-[N-(2,3-dihydro-1,4-benzodioxin-5-yl)-pyrrolidin-3-yl]propanamide;

(S)-N-[N-(2,3-dihydro-1,4-benzodioxin-5-yl)-pyrrolidin-3-yl]butyramide;

(S)-N-[N-(2,3-dihydro-1,4-benzodioxin-5-yl)-pyrrolidin-3-yl]cyclopropane carboxamide;

(R)-N-[N-(2,3-methylenedioxyphen-1-yl)-pyrrolidin-3-yl]-N'-methyl urea;

(R)-N-[N-(2,3-methylenedioxyphen-1-yl)-pyrrolidin-3-yl]-N'-ethyl urea;

(S)-N-[N-(2,3-dihydro-1,4-benzodioxin-5-yl)-pyrrolidin-3-yl]-N'-methyl urea;

(S)-N-[N-(2,3-dihydro-1,4-benzodioxin-5-yl)-pyrrolidin-3-yl]-N'-ethyl urea; and (S)-N-[N-(2,3-dihydro-1,4-benzodioxin-5-yl)-pyrrolidin-3-yl]-N'-n-propyl urea;

or a nontoxic pharmaceutically acceptable salt, hydrate or solvate thereof.

10. A method of treating circadian rhythm-related disorders in a patient in need of such treatment comprising administering to said patient a therapeutic amount of a compound of claim 1.

11. A method of treating sleep disorders in a patient in need of such treatment comprising administering to said patient a therapeutic amount of a compound of claim 1.

12. A composition useful for treating circadian rhythm-related disorders comprising a therapeutic amount of a compound of claim 1 and a suitable amount of a pharmaceutically acceptable carrier.

* * * * *